United States Patent [19]

Quay

[11] Patent Number: 4,687,658

[45] Date of Patent: Aug. 18, 1987

[54] METAL CHELATES OF DIETHYLENETRIAMINEPENTAACETIC ACID PARTIAL ESTERS FOR NMR IMAGING

[75] Inventor: Steven C. Quay, Menlo Park, Calif.

[73] Assignee: Salutar, Inc., Sunnyvale, Calif.

[21] Appl. No.: 657,676

[22] Filed: Oct. 4, 1984

[51] Int. Cl.$^4$ .................... A61K 49/00; A61B 5/05; A61B 6/00

[52] U.S. Cl. .......................................... 424/9; 128/653; 128/654; 436/173; 436/806; 556/40; 556/146; 556/147; 556/148

[58] Field of Search .................... 424/9; 128/653, 654; 556/40, 146, 147, 148; 436/173, 806

[56] References Cited

FOREIGN PATENT DOCUMENTS 8633082 1/1983 Australia .

OTHER PUBLICATIONS

Chemical Abstracts, vol. 101, (1984), 101: 216407q, p. 316.
Chemical Abstracts, vol. 90, (1979), 90: 203450c, p. 567.
Pykett, I., Scientific American, May 1982, pp. 78–88.

*Primary Examiner*—Christine M. Nucker
*Assistant Examiner*—Stephen C. Wieder
*Attorney, Agent, or Firm*—Sprung Horn Kramer & Woods

[57] ABSTRACT

Homologs of Diester-DTPA-Paramagnetic compounds (such as dimethyl acetyl diethylene triamine triacetic acid) provide excellent contrast agents for magnetic resonance imaging (MRI). The magnetic dipole generated by the unpaired electron within the paramagnetic (PM) atom, causes a local reduction in the bulk magnetic field of the MRI system. The resulting shorting of the T1 (spin lattice) relaxation time in the local hydrogen protons within the area of interest, causes an intense "free induction signal" and a corresponding modulation in the collected scanning data. The tissue or organ of interest appears on the MRI display highlighted in white. Background tissue is displayed as darker or lower intensity greys. The ester homologs replace two carboxylic acids to form functional ester groups on the DTPA chelator. The homologs cause the Diester-DTPA-PM contrast agents to go into solution readily, and promotes organ selectivity.

27 Claims, 8 Drawing Figures

METAL CHELATES OF DIETHYLENETRIAMINEPENTAACETIC ACID PARTIAL ESTERS FOR NMR IMAGING

TECHNICAL FIELD

This invention relates to MRI contrast agents, and more particularly to homologs of Ester DTPA-PM contrast agents.

BACKGROUND

Schering (No. 3,129,906 Germany) by Gries, Rosenberg, and Weinstien teaches the incorporation of paramagnetic metals into diethylene triamine pentaacetic acid (DTPA) forming chelates useful as a contrast agent in nuclear magnetic resonance (NMR) imaging. The contrast agent DTPA-(GdIII) as taught by Schering is insoluble in water and requires the addition of cations "C+" (amines such as gulcamine, N-methylglucamine, etc.) as shown below: The charge balance of the Schering DTPA-Gd(III) ion is:

Schering DTPA-GD(III) Charge Balance
C+  C+  DTPA  Gd
+1  +1   −5   +3  = 0

The resulting contrast agent has three ion particles in solution for each paramagnetic atom (a particle to PM ratio of 3:1). A paramagnetic metal with a valence of two, such as Mn, whoud require an additional glucamine ion:

Schering DTPA-Mn(II) Charge Balance
C+    C+  C+  DTPA  Mn
+1 +  +1  +1   −5   +3  = 0 raising the PM to particle ratio to 4:1.

These contrast agents raise the in vivo ion concentration and disturb the local osmolarity balance. The osmolarity is normally regulated at about 300 milliosmols per liter. Increasing the osmolarity with injected ions, causes water to collect within the unbalance region which dilutes the ion concentration.

SUMMARY

It is therefore an object of this invention to probice improved contrast agents for MRI imaging.

It is another object of this invention to provide MRI contrast agents which have a high stability, a low toxicity and is physiologically tolerable.

It is a further object of this invention to provide contrast agents with a higher paramagnetic effect for MRI imaging.

It is a further object of this invention to provide contrast agents in pharmacological form with a low osmolarity.

It is a further object of this invention to provide contrast agents which are in vivo responsive.

It is a further object of this invention to provide contrast agents which are organ selective.

It is a furtehr object of this invention to provide a method of manufacturing such contrast agents.

It is a further object of this invention to provide a method of using such contrast agents.

It is a further object of this invention to provide an MRI system employing such contrast agents.

Briefly, these and other object of the present invention are accomplished by providing a chemically stable physiologically tolerable contrast agent in a pharmacological state, for in vivo use during diagnostic magnetic resonance imaging (MRI). The contrast agent enhances the MRI image of a subject within the MRI scanning magnetic field. A paramagnetic metal ion PM(+Z) having an atomic charge of Z locally affects the MRI scanning magnetic field to reduce the T1 relaxation time of local protons within the subject. The contrast agent contains a triamine chelator DTPA' securely polar bonded around the PM(+Z) ion at a plurality of coordination points, has the form:

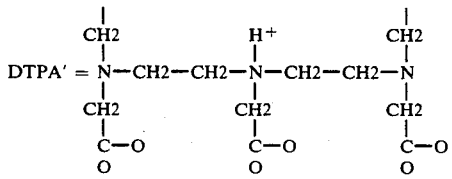

for chemically isolating the PM(+Z) ion from the in vivo environment. A functional ester grop of the form:

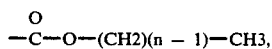

wherein "n" is an integer from 1 to 16 indicating the number of Carbon atoms in the Carbon-Hydrogen portion of the ester group. The functional ester may be a homo-diester or a hetrodiester. The Ester-DTPA'-OM contrast agent is dispensed in a a pharmaceutically acceptable vehicle means such as water. The Carbon-Hydrogen portion to the ester compound becomes associated with water of hydration which increases the paramagnetic strength of the contrast agent. The PM ion may have a valence of +3 and produce a contrast agent molecole of zero net charge. The PM ion may have a valence of +2 and require an inert cation IN having an atomic charge to produce a molecule with a zero net charge. The paramagnetic metal ion PM(+Z) is at least one element selected from the Transistion Elements 24–29 or the Lanthanide Elements 57–71.

BRIEF DESCRIPTION OF THE DRAWING

Further objects and advantages of the present paramagnetic contrast agents, and the method of manufacture and use thereof, will become apparent from the following detailed description and drawing in which:

FIG. 6 is a flow chart showing a method of using the Diester-DTPA-PM paramagnetic contrast agents.

DIESTER-DTPA-PM CONTRAST AGENTS (FIG. 1 (A B C)

Figure 1A:
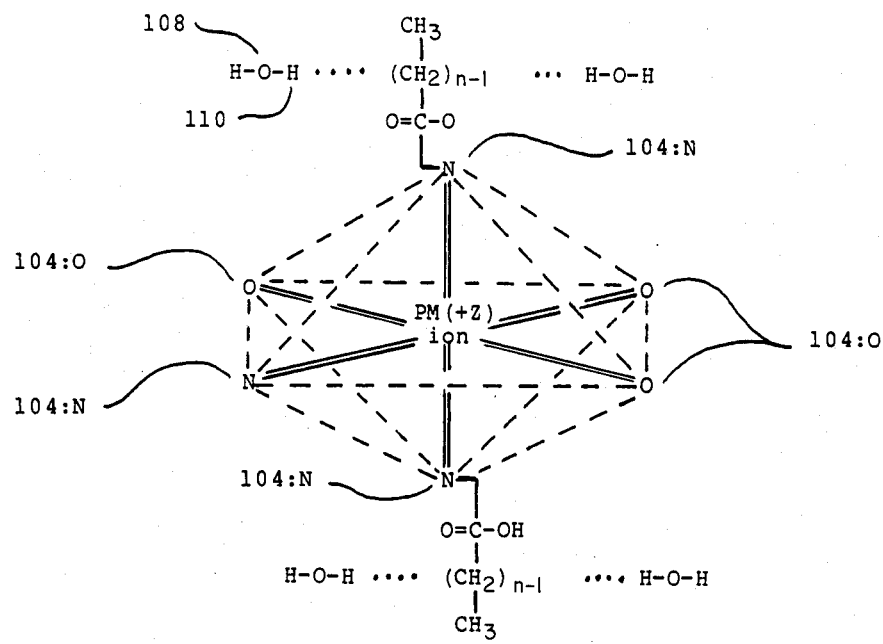
FIG. 1A is a diagram showing the chelate structure and water of hydration of a Diester-DTPA-PM(Z) contrast agent in which Z= +3.

The present paramagnetic contrast agents are ester homologs of the DTPA-PM chelate, having the general chemical name diester acetyl - diethylene triamine triacetic acid (or Diester-DTPA). The probable physical chelation structure of Diester-DTPA-PM is a classic octahedron (8 faces, 6 apexes) as shown in FIG. 1A. The Diester-DTPA homolgs are strong chelators with six polar bond coordination points 104 (three nitrogen points 104:N and three oxygen points 104:O) which enclose the paramagnetic ion PM(Z) on all sides.

Figure 1B:
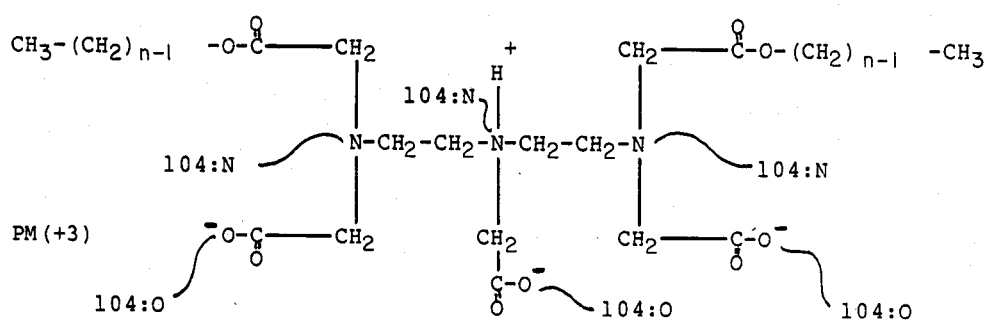
FIG. 1B is a diagram showing the chemical structure of the Diester-DTPA-PM contrast agent of FIG. 1A.

Diester-DTPA-PM has the general chemical structure shown in FIG. 1B. The homologs of Diester-DTPA-PM(Z) have similar structures with a specific number "n" of carbons in the Carbon-Hydrgen portion of the ester group. The number of Carbons in the methylene CH2 chain between the -COO- active group and the terminal methylene —CH3, is "n-1".

Two of the original five DTPA acetic acid groups have become ester groups "E". In general:

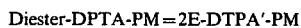
Diester-DPTA-PM=2E-DTPA'-PM where E is a general ester group of the form:

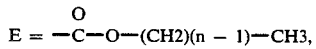
$$E = -\overset{O}{\underset{}{C}}-O-(CH_2)(n-1)-CH_3,$$

and DTPA' is a modification of DTPA of the form:

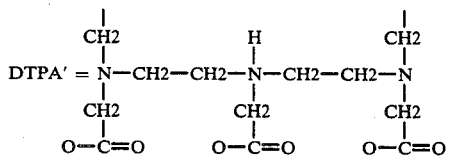

and PM is a paramagnetic metal ion. The elimination of the two acetic acid groups reduces the ion charge of the DTPA chelator from five to three.

Paramagnetic ions having a valence of Z=+3 as shown in FIGS. 1A and 1B, produce a diester contrast agent of the general form:

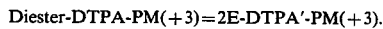
Diester-DTPA-PM(+3)=2E-DTPA'-PM(+3).

This Type III contrast agent has a zero net charge as tabulated below:

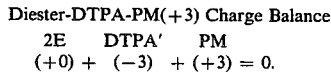
Diester-DTPA-PM(+3) Charge Balance
2E   DTPA'   PM
(+0) + (−3)  + (+3) = 0.

The particle (osmolarity) to paramagnetic (molar relaxivity) ratio for Diester-DTPA-PM(+3) type contrast agents (Z=+3) is 1:1. The Diester-DTPA-PM(Z) contrast agents formed around plus III paramagnetic metals can be prepared in highly concentrated solutions while retaining isotonicity with body fluids. The Schering DTPA-PM(+3) has a particle to paramagnetic ratio of 3:1, and can only be made in isotonic solutions at substantially lower concentrations. Therefore, greater volumes of the Schering DTPA-PM(+3) need by injected into animals or humans to obtain the same paramagnetic effect.

Figure 1C:
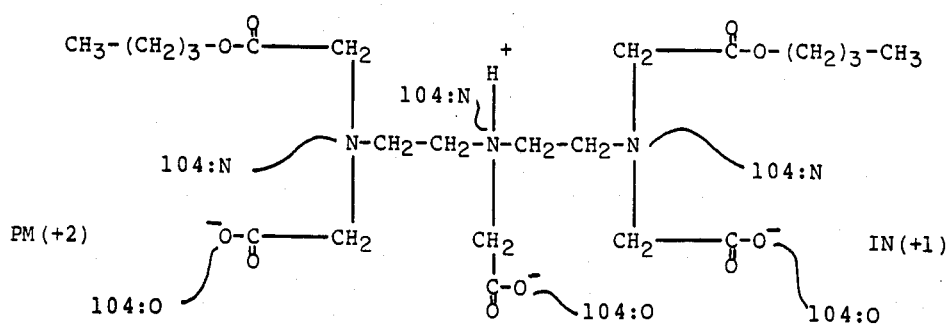
FIG. 1C is a diagram showing the chemical structure of a general Diester-DTPA-PM(Z) contrast agent in which Z= +2.

Paramagnetic ions having a valence of Z=2, produces ester contrast agents of the general form:

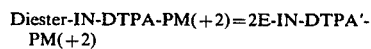
Diester-IN-DTPA-PM(+2)=2E-IN-DTPA'-PM(+2)

where IN is a suitable inert ion, such as a simple mineral salt cation (Na+, Li+, etc.) or an organic ion such as Methyl glucamine or N-methyl glucamine, having a charge of plus one (see FIG. 1C). This Type II contrast agent also has a zero net charge as tabulated below:

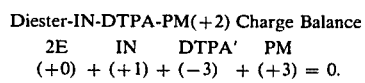
Diester-IN-DTPA-PM(+2) Charge Balance
2E   IN   DTPA'   PM
(+0) + (+1) + (−3) + (+3) = 0.

The particle to paramagnetic ratio for the In-Diester-DTPA-PM(+2) contrast agents is 2:1, producing a low osmoloarity impact.

The above Diester-DTPA-PM Type III and Type II contrast agents have a higher paramagnetic effect than the Schering DTPA-PM. For example, Methyl-DTPA-Gd(III) requires a concentration of only about 1.91 mM to produce a T1 relaxation time of 67 msec (10 MHz field strength, using an RADX). The concentration of Schering DTPA-Gd(III) required to produce a similar result is about 3.16.

Methyl-DTPA-Gd(III) has about twice the paramagnetism of Schering DTPA-Gd(III); and Methyl-DTPA-Fe(III) has about 1.3 times the paramagnetism of Schering DTPA-Fe(III). Possibly the water of hydration 108 (see FIG. 1A) which collects around the ester CH2 chains offers a reliable source of protons (H+) 110 for resonanting with the applied MRI fields. Protons 110 have a high probablity of being present within the local magnetic field of the PM ions. These protons form a class of protons for MRI imaging which is distinct from random in vivo protons. The prolonged association time of bound water 108, and the close proximity of protons 110 to the PM ion, establishes a definite and distinct T1 relaxation time which is longer than the T1 for random protons. As a result, protons 110 provided by the water of hydration appear at a higher intensity in the MRI image.

Figure 2:
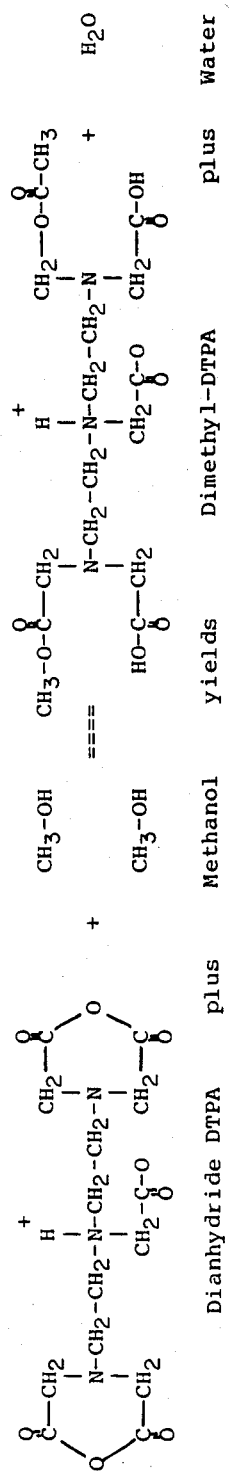
FIG. 2 is a diagram showing the anhydride-methanol production of Dimethyl-DTPA-PM(Z) in which Z= +3.
Figure 3:
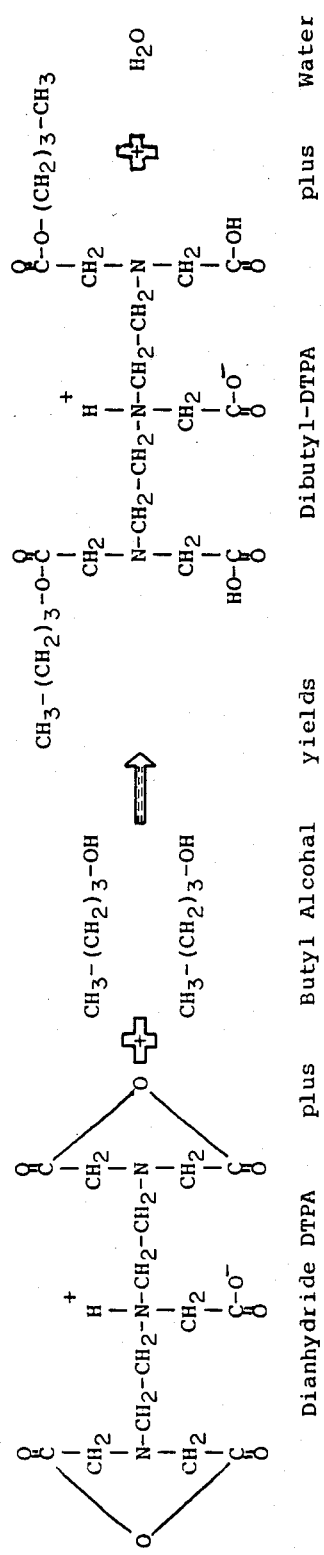
FIG. 3 is a digram showing the anhydride-methanol production of Dibutyl-DTPA-PM(Z) in which Z= +2.
Figure 4:
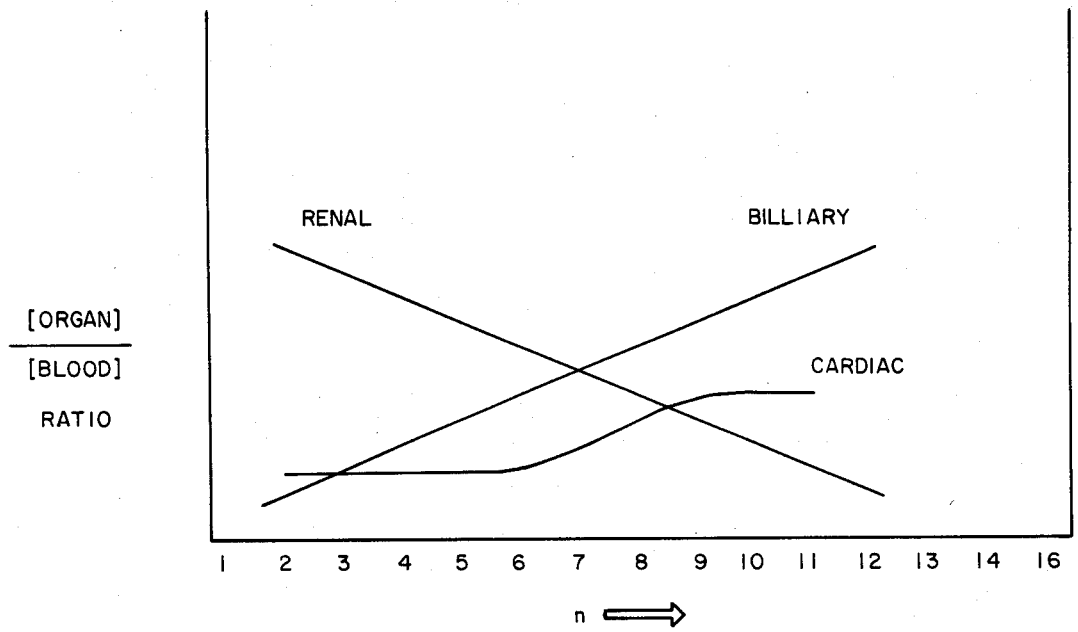
FIG. 4 is a chart showing the organ selectivity of homologs of Diester-DTPA-PM paramagnetic contrast agents.
Figure 5:
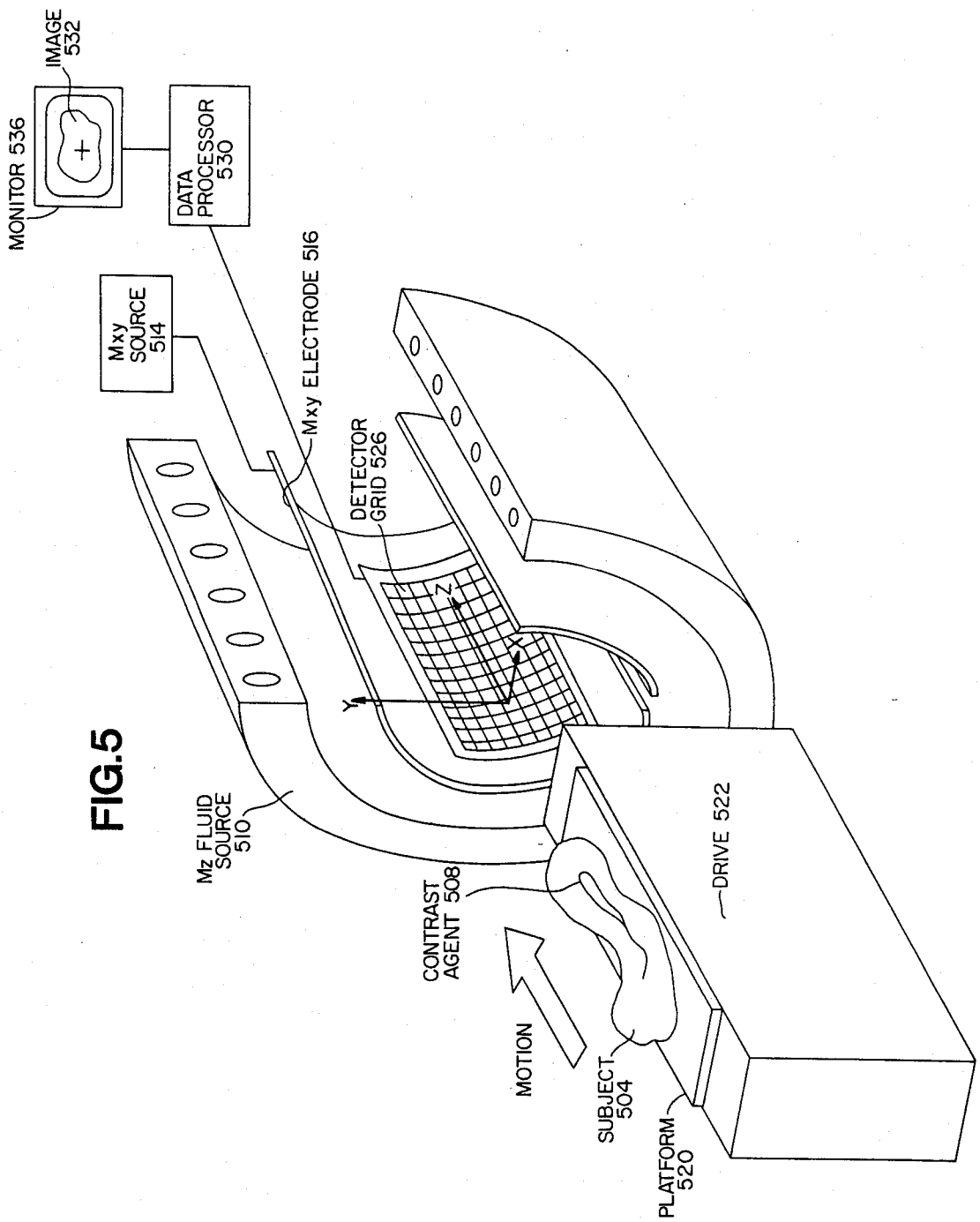
FIG. 5 is a cut-away perspective view of an MRI system showing the motion platform and subject using Diester-DPTA-PM paramagnetic contrast agents.

METHOD OF MANUFACTURE (FIGS. 2 and 3)

A general annydride-diester method is suitable for making each homolog of the ester family of DTPA'-PM contrast agents. In the example below the paramagnetic ion is provided by Fe(III)-(Cl)3, for chelation into dimethyl ester (n=1). However, other paramagnetic ions in other forms may be employed for chelation into other ester homologs.

(Step 1)

FORMATION of Ester-DTPA (see FIG. 2)

Mix 1-5 grams dianhydride DTPA (obtained from Sigma Chemical Co, St Louis, Mo.) into 50-150 mL of pure methanol.

The alcohol forms both the reactant and the solvent for the DTPA anhydride. ratios of alcohol/DTPA are not required, Precise so long as excess alcohol is provided.

(Step 2)

HEAT the solution for several hours (overnight) at reflux temperature, to produce the ester derivative Dimethyl-DTPA (n=1) plus water.

Higher homologs of Diester-DPTA may be formed using the corresponding higher homolog of alcohol for the solvent-reactant. Chloroform may be used as the solvent for higher homologs.

Formation of the Dibutyl-DTPA (n=4) diester homolog is shown in FIG. 3.

(Step 3)
REMOVE the excess alcohol, by vacuum rotary evaporation leaving an Diester-DTPA crystal residue.

(Step 4)
MIX the Diester-DTPA residue in an FeCl3 water solution of stochiometric proportions, to form Diester-DTPA-(Fe+3) plus 3HCl.

Type II metals will require an inert cation (IN) which may be added to the solution at this point.

(Step 5)
REMOVE the HCl
(A) by evaporation using a rotary evaporator.
(B) by neutralization using NaOH or NH3OH.
(C) by chromatograpy using a silica gel column.

(Step 6)
REMOVE the water by vacuum-freezing to form a highly stable form of Diester-DTPA-PM.

(Step 7)
DISPERSE the Ester-DTPA-PM in suitable vehicle to provide a pharmacological form.

Water is a suitable vehicle for dissolving the lower homologs of Diester-DTPA-PM (n less than 10). Higher homologs are hydrophobic and form an emulsion with water. These higher homologs have the same density as water and therefore do not settle out. The isodense character of the homologs of Diester-DTPA-PM permits a wide range of water:homolog ratios.

ESTER FAMILY (n=1 to n=16)

The ester family of DTPA'-PM contrast agents include the homo-diesters (n=n') structure and the hetero-diesters (n not equal to n') structure.

| Name of Ester | n,n' | Properties of Interest |
|---|---|---|
| Methyl-DTPA-PM | 1,1 | Excellent renal |
| Ethyl-DTPA-PM | 2,2 | and blood-brain |
| Propyl-DTPA-PM | 3,3 | barrier constrast |
| Butyl-DTPA-PM | 4,4 | agent. |
| Pentyl-DTPA-PM | 5,5 | Demonstrates renal |
| Hexyl-DTPA-PM | 6,6 | and hepatobiliary |
| Heptyl-DTPA-PM | 7,7 | imaging. |
| Octyl-DTPA-PM | 8,8 | Also shows cardiac |
| Nonyl-DTPA-PM | 9,9 | imaging of infarctions |
| Decyl-DTPA-PM | 10,10 | and ischemic lesions. |
| to | 16,16 | |
| Methyl-Stearyl-DTPA-PM | 1,16 | Passes into the Cardiac system imaging. |

The hetero-diesters have one short CH2 chain (n=1 or more), and one long CH2 chain (n=16 or less). A single long hydrophobic chain, together with the charged DTPA' moiety, renders the chelate an isosteric substitute for fatty acids; and produces substantial tissue levels of the chelate in those organs which have efficient fatty acid uptake systems such as the myocardium.

ORGAN SELECTIVE

The contrast agent is immediately distributed throughout the circulatory system for imaging. The distribution to organs is based on relative blood flow. Organs such as the kidney, brain, liver, and heart receive substantial blood flow; and therefore provide selective images which are correspondingly enhanced.

The higher homologs of Ester-DTPA-PM tend to be less polar and to bind to serum -roteings prolonging their circuilation time. They also tend to be extracted from circulation by the liver and excreted in the hepatobiliary system. These homologs are liver selective and suitable for imaging the liver and hepatobiliary (gall bladder) system.

The lower homologs tend to be more polar and remain in solution longer. They are eventually absorbed by the kidney. These homologs are kidney selective and suitable for imaging the kidney, ureter, and bladder.

The higher homologs are fatty acid analogs and are thus extracted by the heart along with the regular fatty acids. These homologs (n=7 and greater) are cardiac selective and suitable for imaging the cardiac system and cardiac related functions.

STABLE-POWDER STATE

The stable powder state of the Diester-DTPA-PM contrast agents have an indefinite shelf life, and is the preferred state for shipping and storage. The contrast agent in water solution (or other solvent) is packaged in small storage vials, and frozen under a vacuum. The low pressure sublimates the solvent, leaving crystals of the contrast agent. The vial is sealed to prevent entry of external contaminants, and to to preserve the internal vacuum. The resulting freeze-dried, vacuum sealed powder, is highly stable and free from cnvironmental degradation effects.

PHARMACOLOGICAL-SOLUTION STATE

Prior to injection, the stable-powdered contrast agent may be raised to the pharacalogical state by the addition of a suitable solvent such as water, serum, albumin solutions, or saline. A typical injectable composition contains about 10 mg human serum albumin (1 percent USP Parke-Davis) and from about 10 to 500 micrograms of Diester-DTPA-PM material per milliliter of 0.01 M phosphate buffer (pH 7.5) containing 0.9 percent NaCl. The pH of the aqueous solutions may range between 5-9, preferably between 6-8. The storage vial may have twin compartments containing the desired amounts of powdered Diester-DTPA-PM and solvent for a single application. When the seal between the compartments is broken, the Diester-DTPA-PM goes into solution at the desired concentration for immediate use. The Diester-DTPA-PM solution mixes readily with the in vivo fluids.

PARAMAGNETIC EXAMPLES

Paramagnetic material PM may be any paramagnetic element, molecule, ion or compound having a combined valence of "Z". Paramagnetic material PM includes at least one of the following elements:

| Ions of Transition Elements | |
|---|---|
| Cr(III) 24 (Chromium) | Co(II) 27 (Cobalt) |
| Mn(II) 25 (Manganese) | Ni(II) 28 (Nickel) |
| Fe(III) 26 (Iron) | Cu(III) 29 (Copper) |
| Fe(II) 26 (Iron) | Cu(II) 29 (Copper) |
| Ions of Lanthanide Elements | |
| La(III) 57 (Lanthanum) | Gd(III) 64 (Gadolinium) |
| Ce(III) 58 (Cerium) | Tb(III) 65 (Terbium) |
| Pr(III) 59 (Praseodymium) | Dy(III) 66 (Dysprosium) |

| -continued | |
|---|---|
| Nd(III) 60 (Neodymium) | Ho(III) 67 (Holmium) |
| Pm(III) 61 (Promethium) | Er(III) 68 (Erbium) |
| Sm(III) 62 (Samarium) | Tm(III) 69 (Thulium) |
| Eu(III) 63 (Europium) | Yb(III) 70 (Ytterbium) |
| | Lu(III) 71 (Lutetium) |

Gd has the highest paramagnetic property; but is a costly and highly toxic in the free state. Placing the Gd within the chelator produces a physiologically tolerable form of Gd; but also reduces paramagnetic effect of the Gd. The chelate structure tends to shield the paramagnetic ions and prevents close proximity to local H+ protons. Fe and Mn have a high paramagnetic property and excellent physiological tolerence. Both of these paramagnetic ions are normally present in the physiological environment.

GENERAL MRI SYSTEM
(FIG. 5)

Magnetic resonance imaging (MRI) system 500 has two magnetic components which scan subject 504 for obtaining MRI data enhanced by the presence of contrast agent 508. Bulk magnetic field Mz from Z field source 510 causes Paramagnetic particles such as local hydrogen protons within the subject to aline with the Z axiz. Periodic or rotating field Mxy from XY field generator 514 extends between XY electrodes 516. The subject to be scanned is positioned on support platform 520 and moved through the magnetic fields by drive 522. Rotating field Mxy is tuned to cause resonant precession of the local protons within the tissue of interest. Each local proton precesses about the Z axis in respopse to a particular frequency of rotating field Mxy. When rotating field Mxy is removed, the precessing protons decay back into alinement with Mz.

The decay period of the local protons (spin lattice relaxation time T1) varies between organs and between conditions within the same organ. Tumor tissue tends to have a longer T1 than healthy tissue. The presence of the Paramagnetic metal ions PM causes a shortening of the proton T1, without substantially affecting T2 (spin-spin relaxation time). The energy of precession is released forming a free induction signal. Grid detector 526 senses the decay signals which are stored and processed by data processer system 530. to form an image 532 on monitor 536. The metal ion in the contrast agent are not directly imaged by the MRI system.

The imaging system is further disclosed in Scientific American, May 1982, pages 78–88, which disclosure is hereby incorporated by reference.

METHOD OF USE
(FIG. 6)

FIG. 6 shows a method of imaging subject 504 with MRI system 500 employing an paramagnetic contrast agent 508.

(Step 1)
PROVIDING a physiologically tolerable contrast agent 508 in the form: 2E-DTPA-PM(+Z).

If initially in powder form, the 2E-DTPA-PM contrast agent must be dispensed into a suitable carrier vehicle.

(Step 2)
INTRODUCING the 2E-DTPA-PM contrast agent into subject 508 (preferrable by intravenous injection).

(Step 3)
WAITING for the ester functional groups to cooperate with the in vivo environment.

(Step 4)
IMAGING the subject the MRI system 500 to obtain an enhanced MRI image.

Comparison or subtraction imaging, requires an initial step of providing data from a prior MRI imaging, and the final step of subtraction comparing the prior MRI image with the current MRI image. A historical base line image from the subjects file may be employed as the prior image. Alternatively, a current MRI image made without the use of a contrast agent may be employed.

INDUSTRIAL APPLICABILITY

It will be apparent to those skilled in the art that the objects of this invention have been achieved as described hereinbefore by providing an improved physiologically tolerable contrast agents with a high stability, and a low toxicity. The contrast agent has a higher paramagnetic effect due to the ester water of hydration, and a low osmolarity due to the ester bonding. The variability of the ester structure permits a range of vivo response and organ selection.

CONCLUSION

Clearly various changes may be made in the structure and embodiments shown herein without departing from the concept of the invention. Further, the features of the embodiments shown in the various Figures may be employed with the embodiments of the other Figures.

Therefore, the scope of the invention is to be determined by the terminology of the following claims and the legal equivalents thereof.

What is claimed is:

1. A chemically stable physiologically tolerable contrast agent in a solid state, for use in vivo solution during diagnostic magnetic resonance imaging (MRI), to enhance the MRI image of a subject within the MRI scanning magnetic field, comprising:
   a contrast agent of the form:
   E-DTPA-PM,
   where:
   E-DTPA is an ethylene triamine pentaacetic acid chelator in which at least one of the five acetic acid groups has become a functional ester group E of the form:
   $E = -COO-(CH_2)_{n-1}-CH_3$,
   wherein "n" is an integer from 1 to 16 indicating the number of Carbon atoms in the Carbon-Hydrogen portion of the ester group E, for functionally cooperating with the in vivo environment; and
   PM is a paramagnetic metal ion having an atomic charge of +Z, securely chelated at a plurality of coordination points into the E-DTPA chelator to chemically isolate the PM(+Z) ion from the in vivo environnent, for locally affecting the magnetic field of the MRI system;
   whereby the contrast agent causes a reduction in the T1 relaxation time near the region of interest within the subject.

2. The contrast agent of claim 1, wherein the contrast agent is a diester of the form:
   2E-DTPA-PM,
   where:
   2E-DTPA-PM is ethylene triamine pentaacetic acid chelator in which two of the five acetic acid groups have been become a pair of functional ester groups E of the form:

E=—COO—(CH$_2$)$_{n-1}$—CH$_3$, wherein n is an integer from 1 to 16 indicating the number of Carbon atoms in the Carbon-Hydrogen portion of each ester group E1 and E2.

3. The contrast agent of claim 2, wherein Z=+3 and the 2E-DTPA-PM(+3) molecule has a zero net charge.

4. The contrast agent of claim 2, wherein Z=+2 and the general form is:

2E-IN-DTPA-PM(+2), where:

IN is an inert cation of charge +1; and the 2E-IN-DTPA-PM(+2) molecule has a zero net charge.

5. The contrast agent of claim 1, wherein the paramagnetic metal ion PM(+Z) is at least one element selected from the group consisting of:

Cr(III)
Mn(II)
Fe(III)
Fe(II)
Co(II)
Ni(II)
Cu(III)
Cu(II)
La(III)
Ce(III)
Pr(III)
Nd(III)
Pm(III)
Sm(III)
Eu(III)
Gd(III)
Tb(III)
Dy(III)
Ho(III)
Er(III)
Tm(III)
Yb(III)
Lu(III).

6. The contrast agent of claim 1, wherein the paramagnetic metal ion PM(+Z) is at least one element selected from the group consisting of:

Cr(III)
Mn(II)
Fe(III)
Fe(II)
Gd(II)
Co(II)
Ni(II)
Cu(III)
Cu(II).

7. A chemically stable physiologically tolerable contrast agent in a pharmacological state, for in vivo use during diagnostic magnetic resonance imaging (MRI), to enhance the MRI image of a subject within the MRI scanning magnetic field, comprising:

a paramagnetic metal ion PM(+Z) having an atomic charge of Z for locally affecting the MRI scanning magnetic field within the subject to reduce the T1 relaxation time thereof;

a triamine chelator DTPA' securely polar bonded around the PM(+Z) ion at a plurality of coordination points to provide a DTPA'-PM, and having the form:

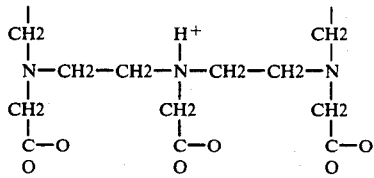

for chemically isolating the PM(+Z) ion from the in vivo environment;

functional group means formed by an ester compound of the form

—COO—(CH$_2$)$_{n-1}$—CH$_3$, wherein "n" is an integer indicating the number of Carbon atoms in the Carbon-Hydrogen portion of the ester compound, for functionally cooperating with the in vivo environment, covalently bonded to the DTPA'-PM chelator forming an Ester-DTPA'-PM contrast agent; and a pharmaceutically acceptable vehicle means for dispersing the Ester-DTPA'-PM contrast agent.

8. The contrast agent of claim 7, wherein the functional group means comprises:

a first ester group having n1 Carbon atoms in Carbon-Hydrogen portion, and covalently bonded to the DTPA'-PM chelator; and a second ester group having n2 Carbon atoms in Carbon-Hydrogen portion, and covalently bonded to the DTPA'-PM chelator;

to form a Diester-DTPA'-PM.

9. The contrast agent of claim 8, wherein n1 and n2 may by any whole integer from 1 to 16.

10. The contrast agent of claim 9, wherein the Diester-DTPA'-PM is a homo-diester in which n1=n2.

11. The contrast agent of claim 9, wherein the Diester-DTPA'-PM is a hetro-diester in which n1 is larger than n2.

12. The contrast agent of claim 7, wherein the paramagnetic metal ion (PM+Z) is at leat one element selected from the group consisting of:

Cr(III)
Mn(II)
Fe(III)
Fe(II)
Co(II)
Ni(II)
Cu(III)
Cu(II)
La(III)
Ce(III)
Pr(III)
Nd(III)
Pm(III)
Sm(III)
Eu(III)
Gd(III)
Tb(III)
Dy(III)
Ho(III)
Er(III)
Tm(III)
Yb(III)
Lu(III).

13. The contrast agent of claim 7, wherein the paramagnetic metal ion (PM+Z) is at least one element selected from the group consisting of:

Cr(III)
Mn(II)
Fe(III)
Fe(II)
Gd(II)
Co(II)
Ni(II)
Cu(III)
Cu(II).

14. The contrast agent of claim 7, wherin $Z=+3$ and the Ester-DTPA'-PM molecule has a zero net charge.

15. The contrast agent of claim 7, wherein $Z=+2$ and the further comprises an inert cation IN having an atomic charge of $+1$ forming a
Ester-IN($+1$)-DTPA'-PM($+2$) molecule with a zero net charge.

16. The contrast agent of claim 7, wherein the vehicle means is a water solution.

17. The contrast agent of claim 16, further comprising water of hydration associated with the Carbon-Hydrogen portion to the ester compound.

18. The contrast agent of claim 7, wherein the paramagnetic metal ion PM($+Z$) is Fe(III).

19. The contrast agent of claim 7, wherein the paramagnetic metal ion PM($+Z$) is Mn(II).

20. The contrast agent of claim 7, wherein the paramagnetic metal ion PM($+Z$) is Co(II).

21. The contrast agent of claim 7, wherein the paramagnetic metal ion PM($+Z$) is Gd(III).

22. The method of imaging a subject with a magnetic resonance imaging (MRI) system employing an paramagnetic contrast agent, comprising the steps of:
PROVIDING a physiologically tolerable contrast agent in the form:
2E-DTPA-PM($+Z$),
where:
2E-DPTA is ethylene triamine pentaacetic acid chelator in which two of the five acetic acid groups have been become a pair of functional ester groups E of the form:
$E = -COO-(CH_2)_{n-1}-CH_3$, wherein n is an integer from 1 to 16 indicating the number of Carbon atoms in the Carbon-Hydrogen portion of each ester group E1 and E2,
for functionally cooperating with the in vivo environment; and
PM($+Z$) is a paramagnetic metal ion having an atomic charge of $+Z$, securely chelated at a plurality of coordination points into the 2E-DTPA chelator to chemically isolate the PM($+Z$) ion from the in vivo environment, for locally affecting the magnetic field of the MRI system;
INTRODUCING the 2E-DPTA-PM contrast agent into the subject;
WAITING for the ester functional groups to cooperate with the in vivo environment; and
IMAGING the subject with the MRI system to obtain a contrast agent enhanced MRI image.

23. The method of imaging a subject as specified in claim 22, wherein the contrast agent is introduced by intravenous injection.

24. The method of imaging a subject as specified in claim 22, further comprising the initial step of dispersing the 2E-DTPA-PM contrast agent into a suitable carrier vehicle.

25. The method of imaging a subject as specified in claim 22, further comprising:
the initial step of providing data from a prior MRI imaging: and
the final step of subtraction comparing the prior MRI image with the current MRI image.

26. The method of imaging a subject as specified in claim 25, wherein the prior MRI image is a base line image.

27. The method of imaging a subject as specified in claim 25, wherein the prior MRI image is not a contrast agent enhanced image.

* * * * *

UNITED STATES PATENT AND TRADEMARK OFFICE
CERTIFICATE OF CORRECTION

PATENT NO. : 4,687,658                    Page 1 of 2

DATED : August 18, 1987

INVENTOR(S) : Steven C. Quay

It is certified that error appears in the above-identified patent and that said Letters Patent is hereby corrected as shown below:

| | |
|---|---|
| Col. 1, line 23 | Delete "GD" and substitute --Gd-- |
| Col. 1, line 30 | Delete "whoud" and substitute --would-- |
| Col. 1, line 46 | Delete "probice" and substitute --provide-- |
| Col. 1, line 61 | Correct spelling of --further-- |
| Col. 1, line 67 | Delete "object" and substitute --objects-- |
| Col. 2, line 24 | Delete "grop" and substitute --group-- |
| Col. 2, line 33 | End of line delete "OM" and substitute --PM-- |
| Col. 2, line 44 | Correct spelling of --Transition-- |
| Col. 2, line 64 | Correct spelling of --diagram-- |
| Col. 3, line 3, 28; Col. 5, line 4; Col. 11, line 40; Col. 12, line 16 | Delete "DPTA" and substitute --DTPA-- |
| Col. 3, line 15 | Correct spelling of --homologs-- |
| Col. 3, line 22 | Correct spelling of --Hydrogen-- |
| Col. 4, line 2 | Delete "by" and substitute --be-- |
| Col. 4, line 52 | Correct spelling of --anhydride-- |
| Col. 6, line 6 | Delete "-roteings" and substitute --proteins-- |
| Col. 6, line 7 | Correct spelling of --circulation-- |
| Col. 6, line 32 | Correct spelling of --environmental-- |
| Col. 7, lines 26, 41 | Delete "Paramagnetic" and substitute --paramagnetic-- |
| Col. 7, line 34 | Delete "respopse" and substitute --response-- |

UNITED STATES PATENT AND TRADEMARK OFFICE
CERTIFICATE OF CORRECTION

PATENT NO. : 4,687,658

DATED : August 18, 1987

INVENTOR(S) : Steven C. Quay

It is certified that error appears in the above-identified patent and that said Letters Patent is hereby corrected as shown below:

Col. 8, line 55          Before "Z" delete "+"
Col. 8, line 58          Correct spelling of --environment--
Col. 11, line 11         Correct spelling of --wherein--

Signed and Sealed this

Third Day of May, 1988

*Attest:*

DONALD J. QUIGG

*Attesting Officer*         *Commissioner of Patents and Trademarks*